United States Patent
Lamberti et al.

(10) Patent No.: US 11,262,342 B2
(45) Date of Patent: Mar. 1, 2022

(54) WASTE MATERIAL ANALYSIS SYSTEM

(71) Applicant: Accenture Global Solutions Limited, Dublin (IE)

(72) Inventors: Corinna Lamberti, London (GB); Katherine Goldklang, London (GB); Robert Riley, London (GB)

(73) Assignee: Accenture Global Solutions Limited, Dublin (IE)

(*) Notice: Subject to any disclaimer, the term of this patent is extended or adjusted under 35 U.S.C. 154(b) by 817 days.

(21) Appl. No.: 15/648,002

(22) Filed: Jul. 12, 2017

(65) Prior Publication Data

US 2019/0017982 A1    Jan. 17, 2019

(51) Int. Cl.
  *G01N 33/18*    (2006.01)
  *G01N 21/359*   (2014.01)
  *G06N 20/00*    (2019.01)

(52) U.S. Cl.
  CPC ........... *G01N 33/18* (2013.01); *G01N 21/359* (2013.01); *G06N 20/00* (2019.01)

(58) Field of Classification Search
  CPC .................................................. G01N 21/359
  See application file for complete search history.

(56) References Cited

U.S. PATENT DOCUMENTS

| | | | | |
|---|---|---|---|---|
| 2009/0211150 A1* | 8/2009 | Wu | ............................ | C11B 1/10 44/308 |
| 2016/0097676 A1* | 4/2016 | Kurasawa | ............ | A61B 5/1495 702/104 |
| 2017/0091637 A1* | 3/2017 | Chae | ....................... | G06N 5/048 |
| 2017/0256003 A1* | 9/2017 | Isaacson | .............. | G07G 1/0009 |
| 2017/0292908 A1* | 10/2017 | Wilk | ..................... | G01J 3/0272 |

FOREIGN PATENT DOCUMENTS

| EP | 2215455 | 8/2010 |
|----|---------|--------|
| WO | 2012/118212 | 9/2012 |

OTHER PUBLICATIONS

Machine translation for WO 2012/118212 (Year: 2012).*
'en.wikipedia.org'[online], "Machine Learning," Mar. 24, 2004, [retrieved on Jun. 9, 2017], Retrieved from the Internet: URL< https://en.wikipedia.org/wiki/Machine_learning >, 12 pages.
'en.wikipedia.org' [online], "Sludge," Jun. 18, 2004, [retrieved on Jul. 10, 2017], Retrieved from the Internet: URL< https://en.wikipedia.org/wiki/Sludge >, 2 pages.

(Continued)

*Primary Examiner* — John E Breene
*Assistant Examiner* — Jeffrey C Morgan
(74) *Attorney, Agent, or Firm* — Fish & Richardson P.C.

(57) ABSTRACT

Methods, systems, and apparatus, including computer programs encoded on computer storage media, for molecular content analysis. One of the methods includes receiving molecular content data that indicates a molecular content of a portion of a batch of sludge; determining, by a machine learning module included in the system using the molecular content data and multiple parameters, a predicted value for a property of the portion of the batch of sludge; and providing the predicted value for the property of the portion of the batch of sludge.

21 Claims, 3 Drawing Sheets

(56) References Cited

OTHER PUBLICATIONS

'en.wikipedia.org' [online], "Blockchain," Dec. 22, 2013, [retrieved on Jul. 10, 2017], Retrieved from the Internet: URL< https://en.wikipedia.org/wiki/Blockchain >, 18 pages.
EP Search Report in in European Application 18169572.7, dated Sep. 26, 2018, 8 pages.
Skvaril et al., "Applications of near-infrared spectroscopy (NIRS) in biomass energy conversion processes: a review," Applied Spectroscopy Reviews, Jan. 31, 2017, vol. 52, No. 8 675-728, 86 pages.
EP Office Action in European Application No. EP 18169572.7, dated Apr. 1, 2020 ,7 pages.

* cited by examiner

WASTE MATERIAL ANALYSIS SYSTEM

BACKGROUND

Wastewater processing plants may product batches of waste material, e.g., sludge. The sludge may be a semi-solid material that contains water and other minerals.

SUMMARY

A sludge analysis system processes data that indicates a molecular content of a batch of sludge. The sludge may be a semi-solid slurry that is created from waste material, e.g., wastewater or the output of a product creation process. The sludge analysis system uses the data to predict a value of a property of the batch of sludge. For instance, the sludge analysis system may use the predicted value to customize a treatment process for the batch of sludge, predict a destination or use for the batch of sludge, determine a recommended destination or use, or predict an amount of usable material included in the batch of sludge that can be used for another process.

A predicted use for a batch of sludge may indicate another process, such as farming or bio-gas production, that is most likely to receive the greatest benefit from the batch of sludge given the molecular content of the batch of sludge. For instance, the sludge analysis system may determine a predicted use of "farming" for a batch of sludge that includes a high percentage of organic materials and a medium to low percentage of dry matter, which indicate good fertilization properties. The sludge analysis system may determine a predicted use of a "waste to energy" or "biogas processing" for a batch of sludge that includes organic materials and a high percentage of dry matter. A predicted or recommended destination can be a particular entity that uses the batch of sludge, such as a particular farm or a particular waste to energy plant.

In some implementations, the sludge analysis system may determine a predicted value for a property that represents a quality or another property for a commodity trading platform. For instance, the sludge analysis system may determine a customized treatment process for a batch of sludge based on a predicted destination of the batch of sludge given a type of entity, e.g., a farmer, that can acquire the batch of sludge using the commodity trading platform. The sludge analysis system may use the molecular content of the batch of sludge, a source of the batch of sludge, the predicted destination, or a combination of two or more of these, to determine the predicted property.

In general, one innovative aspect of the subject matter described in this specification can be embodied in methods that include the actions of receiving molecular content data that indicates a molecular content of a portion of a batch of sludge; determining, by a machine learning module included in the system using the molecular content data and multiple parameters, a predicted value for a property of the portion of the batch of sludge; and providing the predicted value for the property of the portion of the batch of sludge. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. The method may include receiving an actual value for the property of the batch of sludge; and updating, by the machine learning module, at least one of the parameters using the actual value for the property of the batch of sludge. Receiving the molecular content data that indicates the molecular content of the batch of sludge may include receiving, from a near infrared spectrometer, near-infrared spectroscopy data. A system may include a near infrared spectrometer. The method may include scanning, by the near infrared spectrometer, the batch of sludge to determine the molecular content data.

In some implementations, determining, by the machine learning module included in the system using the molecular content data and the multiple parameters, the predicted value for the property of the batch of sludge may include determining, in parallel by the machine learning module for each of two or more properties of the batch of sludge, a predicted value for the respective property. Determining, in parallel by the machine learning module for each of the two or more properties of the batch of sludge, the predicted value for the respective property may include determining, for each of the two or more properties of the batch of sludge using regression analysis, the predicted value for the respective property. Determining, in parallel by the machine learning module for each of the two or more properties of the batch of sludge, the predicted value for the respective property may include determining, for each of the two or more properties of the batch of sludge using non-linear classification, the predicted value for the respective property. Determining, by the machine learning module included in the system using the molecular content data and the multiple parameters, the predicted value for the property of the batch of sludge may include determining the predicted value for the property of the batch of sludge using the molecular content data, the multiple parameters, and one or more potential uses for the batch of sludge.

In some implementations, providing the predicted value for the property of the batch of sludge may include providing, to a treatment module, the predicted value for the property of the batch of sludge to cause the treatment module to determine a recommended treatment process for the batch of sludge given the predicted value for the property of the batch of sludge and one or more potential uses for the batch of sludge. Receiving the actual value for the property of the batch of sludge may include receiving the actual value for the property of the batch of sludge after a treatment system processes the batch of sludge using the recommended treatment process. The method may include determining, using the molecular content data, a recommended potential use for the batch of sludge. Providing, to the treatment module, the predicted value for the property of the batch of sludge may include providing, to the treatment module, the recommended potential use and the predicted value for the property of the batch of sludge to cause the treatment module to determine a recommended treatment process for the batch of sludge given the predicted value for the property of the batch of sludge and one or more potential uses for the batch of sludge. Determining, using the molecular content data, the recommended potential use for the batch of sludge may include determining, using the predicted value for the property of the batch of sludge, the recommended potential use for the batch of sludge. The method may include determining, by the treatment module, the recommended treatment process for the batch of sludge given the predicted value for the property of the batch of sludge and the one or more potential uses for the batch of sludge.

In some implementations, determining, by the machine learning module included in the system using the molecular content data and the multiple parameters, the predicted value for the property of the batch of sludge may include determining, by the machine learning module, the predicted value using, as input to the machine learning module, characteristics of a potential purchaser, environmental parameters, or both. The environmental parameters may include at least one of: environmental parameters of a treatment system; environmental parameters for a storage facility at which the batch of waste material is located; environmental parameters for a storage facility at which the batch of waste material will be located prior to delivery to a potential destination; or environmental parameters during transportation. The characteristics of a potential purchaser may include at least one of: environmental parameters for the potential purchaser; characteristics of how a batch of waste material will be used by the potential purchaser; or desired waste material properties for the potential purchaser. Determining, by the machine learning module included in the system using the molecular content data and the multiple parameters, the predicted value for the property of the batch of sludge may include determining at least one of: a predicted value for a percentage of dry matter of the batch of sludge; a predicted value for a percentage of a primary material included in the batch of sludge; a predicted value for a percentage of volatile solids included in the batch of sludge; a predicted value for a percentage of biogas material included in the batch of sludge; a predicted value for a percentage of organic matter included in the batch of sludge; a predicted value for a percentage of phosphorus included in the batch of sludge; a predicted value for a percentage of zinc included in the batch of sludge; or a predicted value for a percentage of material included in the batch of sludge that can be reused.

In some implementations, providing the predicted value for the property of the batch of sludge may include generating instructions for presentation of the predicted value for the property of the batch of sludge in a user interface. Receiving the actual value for the property of the batch of sludge may include receiving data indicating user input of the actual value for the property of the batch of sludge. Generating the instructions for presentation of the predicted value for the property of the batch of sludge in a user interface may include generating the instructions for presentation of a user interface that includes a filter option to enable a user to view details about multiple different batches of sludge, including the batch of sludge, and to filter details about batches of sludge using the predicted values for the property of the respective batch of sludge. Generating instructions for presentation of the predicted value for the property of the batch of sludge in a user interface may include enabling a user to select the batch of sludge for purchase. Generating instructions for presentation of the predicted value for the property of the batch of sludge in a user interface may include enabling a user to select the batch of sludge for purchase using a blockchain smart contract.

The subject matter described in this specification can be implemented in various embodiments and may result in one or more of the following advantages. In some implementations, determining a recommended treatment process using a predicted value of a property for a batch of waste material can reduce treatment processing time, reduce materials used during treatment processes, optimize treatment processing, e.g., for a recommended use or a recommended destination, or a combination of two or more of these. In some implementations, the systems and methods described below can reduce treatment costs, optimize waste material delivery and trading, reduce a quantity of waste material delivered to landfills, or a combination of two or more of these.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
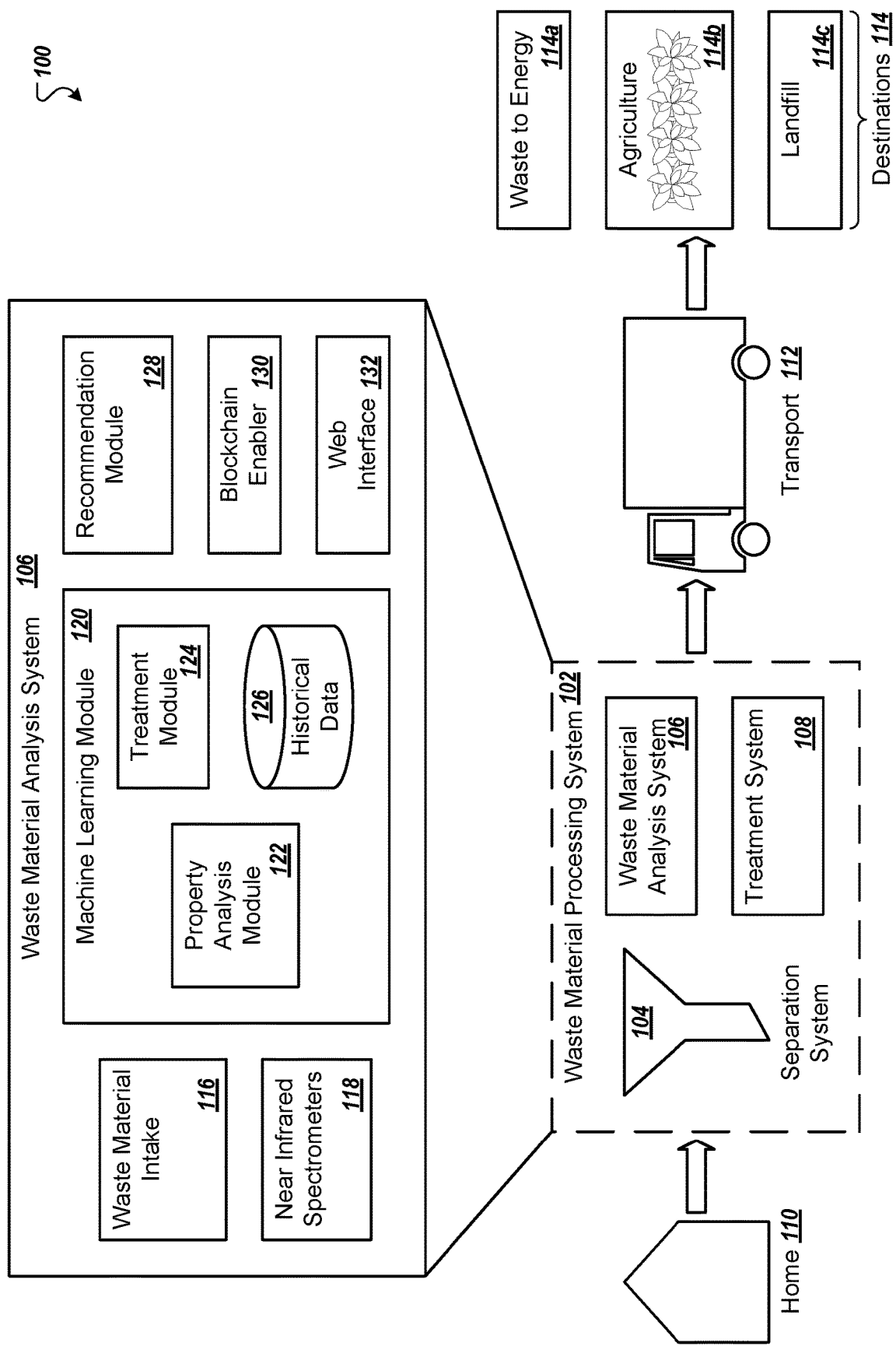
FIG. 1 depicts an example of an environment that includes a waste material processing system that analyzes waste material, such as sludge.

FIG. 1 depicts an example of an environment 100 that includes a waste material processing system 102 that analyzes waste material, such as sludge. For example, the waste material processing system 102 may receive the waste material from a home 110, a factory, e.g., as waste from products that are being built, or a restaurant. The waste material processing system 102 may use one or more of a separation system 104, a waste material analysis system 106, and a treatment system 108 to process the waste material for reuse at a destination 114.

For example, the waste material analysis system 106 may process data about batches of waste material received from the separation system 104 to determine properties of the material included in the batches of waste material. The waste material analysis system 106 may determine recommended treatment processes for each of the batches and provide the treatment system 108 data about those treatment processes, e.g., instructions to cause the treatment system 108 to execute those treatment processes.

After processing a batch of waste material, the waste material processing system 102 provides the processed waste material to a transport system 112 that delivers the processed waste material to a destination 114. The transport system 112 may be any appropriate type of transport system, e.g., using vehicles, ships, planes, or a combination of two or more of these. The destinations 114 may include a waste to energy system 114*a*, agriculture 114*b*, e.g., a farm, or a landfill 114*c*.

The waste material analysis system 106 may include a waste material intake 116, one or more sensors, e.g., one or more near infrared spectrometers 118, or both. For instance, the waste material intake 116 may receive material from the separation system 104. The material may be part of a batch of waste material or an entire batch of waste material.

The near infrared spectrometers 118 captures molecular content data for the material received in the waste material intake 116. For example, the near infrared spectrometers 118 may capture near-infrared spectroscopy data that indicates molecular content properties of the material. In some implementations, the waste material analysis system 106 may include other types of sensors that can capture molecular content data for the material received in the waste material intake 116. The molecular content data may indicate average property values, minimum property values, maximum property values, or a combination of two or more of these, for an entire batch of waste material or a portion of a batch of waste material. The waste material may be sludge.

A machine learning module 120, included in the waste material analysis system 106, receives the molecular content data. The machine learning module 120 processes the molecular content data to determine one or more predicted values for properties of the batch of waste material. The predicted values may be predicted minimum values for a batch of waste material, predicted average values for a batch of waste material, predicted maximum values for a batch of waste material, or a combination of two or more of these.

For instance, a property analysis module 122 may use historical data 126 and the molecular content data to determine a predicted value for at least one of the properties of the batch of waste material. The predicted value may be a predicted value after treatment of the batch of waste material, a predicted value for the batch of waste material before delivery of the batch of waste material to one of the destinations 114, a predicted value for the batch of waste material upon delivery of the batch of waste material to one of the destinations 114, a predicted sale value for the batch of waste material, a predicted value for the batch of waste material after one of the destinations 114 uses the batch of waste material, or a combination of two or more of these. In some examples, the machine learning module 120 may determine multiple predicted values, e.g., for different stages of the batch of waste material. The predicted value may be a maximum value, a minimum value, or an average value for the batch of waste material.

When the predicted value is a predicted value after treatment of the batch of waste material, the property analysis module 122 predicts how a treatment process may change one or more properties of the batch of waste material. The property analysis module 122 may use a potential use of the batch of waste material at one of the destinations 114 to predict the value of a property that affects the potential use, e.g., for a property that indicates a likelihood that the batch of waste material can be used for the potential use. For example, the property analysis module 122 may predict a percentage of organic material that will be included in a batch of waste material when an intended or recommended use is farming. The property analysis module 122 may predict a percentage of biogas material that will be included in a batch of waste material when an intended or recommended use is for a waste to energy process.

The machine learning module 120 or a recommendation module 128 may determine a recommended use, recommended destination, or both, for a batch of waste material, e.g., in addition to or separate from the predicted value of the property. The machine learning module 120 may use the recommended use, recommended destination, or both, to determine the predicted value of the property. For example, when a batch of waste material has a high average amount of organic material, the machine learning module 120 may determine a recommended use of "farming" for an "agricultural" destination 114b. The machine learning module 120 may determine a current value of organic material included in the batch of waste material, e.g., as a percentage or volume.

The machine learning module 120 may predict a value for a property of the batch of waste material before the batch of waste material is delivered to one of the destinations 114. The predicted value before delivery may be a predicted value before the batch of waste material is transported 112 to a destination 114, before the batch of waste material is placed on a transport vehicle, or another time before transport 112. The predicted value may be a value for the batch of waste material after treatment processing and before delivery. The predicted value may be a value for a batch of waste material that will not have treatment processing or that will not have any additional treatment processing, e.g., after the waste material analysis system 106 receives the molecular content data and determines the predicted value. For instance, the waste material analysis system 106 may perform multiple predictions of values for properties of a batch of waste material at different stages of processing: before treatment, e.g., to determine a recommended treatment process, during treatment, after treatment, after a batch of waste material has been at a waste material processing system 102 without any processing, e.g., and is in a storage facility, immediately before a batch of waste material is loaded for transport, or a combination of two or more of these.

The machine learning module 120 may predict the value of a property, e.g., organic material, using the current value and the recommended use. The predicted value may be a predicted value after treatment. In some examples, the machine learning module 120 may use both the property analysis module 122 and a treatment module 124 when determining the predicted value for the property. For instance, the property analysis module 122, or another module in the machine learning module 120, may determine a recommended use for the batch of waste material using the molecular content data as input to the property analysis module. The treatment module 124 may use the recommend use and molecular content data as input to determine a recommended waste material treatment to process the batch of waste material. The treatment module 124 may determine a recommended waste material treatment that will increase, decrease, or both, one or more properties of the waste material to improve the waste material for the recommended use, for use at the recommended destination, or both. The treatment module 124 or the property analysis module 122 may determine the predicted value for the property. For instance, the treatment module 124 may determine the predicted property when determining the recommended waste material treatment. In some examples, the property analysis module 122 may use the recommended waste material treatment, e.g., as input, to determine the predicted value.

The machine learning module 120 may predict a value for a property of the batch of waste material upon delivery of the batch of waste material to one of the destinations 114. For instance, the value for the property may account for any changes in the batch of waste material during processing, transportation, other stages through which the batch of waste material proceeds until the batch of waste material is delivered to one of the destinations 114, or a combination of two or more of these. In some examples, the property may be a predicted percentage of dry matter. The machine learning module 120 may use current weather conditions or predicted weather conditions to determine the predicted value for the dry matter percentage. In some examples, the machine learning module 120 may use a humidity level, a predicted chance of rain, or both, to determine the predicted percentage of dry matter for the batch of waste material. In some implementations, the property may be a cost for the batch of waste material such that the predicted value indicates a predicted sale value. In some implementations, the property may be a percentage of volatile solids or biogas material that will be included in the batch of waste material upon delivery.

Some example properties for a predicted value for a property of the batch of waste material after delivery of the batch of waste material to one of the destinations 114 include volume, volatile solids, biogas materials, organic matter, dry matter, or a combination of two or more of these. The value of the property may be after the batch of waste material is used at a destination 114, while the batch of waste material is being used at a destination 114, or another time after the batch of waste material is delivered. A volume may change when the batch of waste material absorbs or releases moisture, gas, or another material. A percentage of volatile solids may change as the materials in the batch of waste material change in temperature, emit moisture or other material, or otherwise change during processing, transportation, delivery, or a combination of two or more of these. A percentage of organic matter may change as oxygen or another element reacts with the material included in the batch of waste material. In some implementations, the predicted value may be a predicted sale value or a predicted cost for the batch of waste material upon delivery of the batch of waste material. One or more of these properties may change during processing, transportation, delivery, or a combination of two or more of these. In some examples, the machine learning module 120 may determine multiple predicted values for different properties. When the waste material analysis system 106 determines multiple different predicted values, the corresponding actual values may be measured at the same time, different times, or a combination of both.

The machine learning module 120 may use the molecular content data, the historical data 126, or both, as input. For example, the machine learning module 120 may initially perform a training process using the historical data 126 and update one or more parameters of the machine learning module 120 during training. The historical data 126 may include predicted values and actual values for sets of molecular content data. The machine learning module 120 may use a supervised learning process to update the parameters for the machine learning module 120 using the historical data 126. In some implementations, the historical data 126 may include treatment process data that indicates a treatment process used for a batch of waste material and corresponding predicted and actual values for the batch of waste material. In these implementations, the machine learning module 120 may use the historical data 126 to adjust the parameters to cause the machine learning module 120 to predict a recommended treatment process for a batch of waste material. The machine learning module 120 may later, e.g., during run-time, use the molecular content data to determine a predicted value.

In some implementations, the machine learning module 120 may use only the molecular content data as input and the historical data 126 may represent parameters determined by the machine learning module 120 to represent a machine learning algorithm used to analyze the input molecular content data. For instance, the machine learning module 120 may update the historical data 126 using a predicted value for a property and an actual value for a property, e.g., as part of a feedback process. The machine learning module 120 may receive the actual value for the property after a treatment process, e.g., from the near infrared spectrometers 118 or other sensors that measures the value, during transport 112, or after delivery to one of the destinations 114. The machine learning module 120 may use the predicted value and the actual value to update the parameters, e.g., the historical data, during a training process.

The machine learning module 120 may use parameters for any appropriate artificial intelligence process to analyze the molecular content data and determine the predicted value or the predicted values. In some implementations, the machine learning module 120 may use parameters for a non-linear classification of the molecular content data to determine the predicted value. The machine learning module 120 may use parameters for regression analysis of the molecular content data to determine the predicted value. Some examples of models that include the parameters include support vector machines, linear regression models, and random forest modelling. A type of model used for the parameters of the machine learning module 120 may be selected to balance analysis speed of the machine learning module 120, e.g., the time required by the machine learning module 120 to determine a predicted value after receiving molecular content data, and accuracy of the machine learning module 120. For instance, the machine learning module 120 may use parameters that represent a support vector machine or a random forest model to improve an accuracy of the predicted value. In some implementations, the machine learning module 120 may use parameters for random forest modelling to allow the machine learning module 120 to analyze multiple decision trees in parallel.

In some implementations, the property analysis module 122 and the treatment module 124 are the same model. For instance, a single model may use the parameters to determine at least two of a recommended treatment process, a recommended use, a recommended destination, and one or more predicted values for properties of a batch of waste material.

In some implementations, the recommendation module 128 can be part of or included in the machine learning module 120. For instance, a single module may determine the predicted value, the recommended treatment process, and the recommended use. In some implementations, a single module may determine the recommended treatment process and the recommended use.

The recommendation module 128 may use the predicted value for the property of the batch of sludge, the molecular content data, or both, to determine a recommended use, a recommended destination, or both, for the batch of waste material. For instance, the property analysis module 122 may determine the predicted value for the batch of waste material using the molecular content data as input. The recommendation module 128 receives the predicted value and uses the predicted value as input, potentially with the molecular content data, to determine the recommended use, the recommended destination, or both.

A recommended use may be a particular type of process or system in which the batch of waste material can be used. For instance, recommended uses may include waste to energy processes, agriculture, or manufacturing.

A recommended destination may be a particular system that uses a process that can include the batch of waste material. For example, while a recommended use may be agriculture, a recommended destination may be farm A or farm B.

In some implementations, the recommendation module may determine a ranked list of recommended uses, a ranked list of recommended destinations, or both. The ranked list of recommended destinations can include a first destination that has a first use, followed by a second destination that has a second use, and then a third destination that also has the first use. For example, the ranked list of destinations may include farm A followed by energy plant A and then farm B. A ranked list of recommended uses may include agriculture and then waste to energy.

The waste material analysis system 106 may use the ranked list of recommended uses, the ranked list of recommended destinations, or both, to determine the recommended waste material treatment. In some examples, the waste material analysis system 106 may generate instructions for presentation of one or both ranked lists in a user interface.

The recommendation module 128 may use data that indicates properties of a potential destination as input. For instance, the recommendation module 128 may use data that indicates properties for the destinations 114 when determining a single recommended destination or a ranked list of recommended destinations. In some examples, the recommendation module 128 may use the data that indicates properties for the potential destination during a training process during which parameters of the recommendation module 128 are updated based on molecular content data as input and output that identifies particular recommended destinations. Use of molecular content data, e.g., a predicted value or a set of molecular content data for multiple properties of a batch of waste material, as input along with properties for the destinations, e.g., properties that indicate how waste material will be used or desired waste material properties for the destination, may allow the recommendation module 128 to be more robust given potential changes to the properties for the destinations over time, e.g., without necessarily requiring additional training of the recommendation module 128.

In some implementations, the treatment module 124 uses data from the recommendation module 128 to determine a recommended treatment process. For instance, the treatment module 124 may determine a treatment process with a highest likelihood of optimizing a batch of waste material for a particular use, a particular destination, or both.

In some implementations, the property analysis module 122 may determine a particular predicted value based on a recommended use, a recommended destination, or both. For example, the property analysis module 122 can use, as input, the recommended use, the recommended destination, or both, to determine the predicted value. When the recommended use is agriculture, the property analysis module 122 may determine a minimum amount of organic material, a maximum amount of heavy metals, or both, that will likely be included in a batch of waste material. In some examples, when the recommended use is waste to energy, the property analysis module may determine an average amount of biogas material, primary material included in the waste material, a maximum amount of heavy metals, or a combination of two or more of these.

The waste material analysis system 106 can include a blockchain enabler 130 that provides third party systems with information about a batch of waste material, e.g., the predicted value or molecular content data or both, create contracts with third party systems for delivery of a batch of waste material, or both. For example, the blockchain enabler 130 may store, in a distributed blockchain database, the information about a batch of waste material. The information about a batch of waste material may include the predicted value, the molecular content of a batch of waste material, e.g., before or after treatment processing or both, a source of the batch of waste material, or other information about the batch of waste material.

When the recommendation module 128 determines a recommended use, a recommended destination, or both, the blockchain enabler 130 can store data about the recommended use, the recommended destination, or both. This may allow the blockchain enabler 130 to provide potential destinations, e.g., recommended destinations, with information about a batch of waste material. For instance, the blockchain enabler 130 may determine that given the recommended use, the recommended destination, or both, a particular destination can likely use a corresponding batch of waste material. The blockchain enabler 130 may provide the particular destination, e.g., a computer for the particular destination, with the information about the batch of waste material to allow the particular destination to confirm whether the corresponding batch of waste material should be delivered to the particular destination.

Upon receipt of confirmation data indicating that the corresponding batch of waste material should be delivered to the particular destination, the blockchain enabler 130 stores, in the distributed blockchain database, data that indicates that the corresponding batch of waste material should be delivered to the particular destination. The data may indicate transportation type for the delivery and other delivery details.

The waste material analysis system 106 may use any appropriate system to provide a third party systems with information about a batch of waste material. In some implementations, the waste material analysis system may use a web interface 132 to provide information about a batch of waste material. The web interface 132 may provide, to a third party system, instructions that cause presentation of an interface that includes the information about the batch of waste material. The third party system can present the interface in a web browser or another application.

In some implementations, the waste material analysis system 106 may receive the molecular content data that indicates a molecular content of a batch of waste material, or a portion of a batch of waste material, from a device that is not included in the waste material analysis system 106. For instance, the waste material analysis system 106 may be physically located separate from a physical location for the waste material processing system 102. The waste material analysis system 106 may receive the molecular content data from a sensor, e.g., one of the near infrared spectrometers 118, located at the separate waste material processing system 102 or at another physical location at which the batch of waste material is located.

The waste material analysis system 106 may receive the molecular content data from a mobile application, e.g., installed on a mobile device. For example, the mobile device may receive the molecular content data from a sensor and provide the molecular content data to the waste material analysis system 106. In these implementations, the waste material analysis system 106 may be a cloud service that analyzes the molecular content of the waste material. The waste material analysis system 106 may provide the mobile device with a recommended treatment process, data about the molecular content of the waste material, or other data, e.g., a recommended sale price for the waste material.

When the near infrared spectrometers 118 are not included in the waste material analysis system 106, the machine learning module 120, and the waste material analysis system 106, may receive the molecular content data from the near infrared spectrometers 118 using a network interface. The network interface may be part of or used by the web interface 132. For instance, the waste material analysis system 106 may include a network interface that receives the molecular content data from the near infrared spectrometers 118, or other sensors, using a network protocol.

In some implementations, the waste material analysis system 106 may include an application programming interface (API) that receives the molecular content data from an external system, e.g., that includes the near infrared spectrometers 118 or other sensors. The API can allow the waste material analysis system 106 to communicate with other systems, e.g., to receive molecular content data, send treatment recommendations, send predicted values for properties, or a combination of two or more of these.

The waste material analysis system 106 is an example of a system implemented, at least in part, as computer programs on one or more computers in one or more locations, in which the systems, components, and techniques described in this document are implemented. The mobile devices may include personal computers, mobile communication devices, and other devices that can send and receive data over a network. The network (not shown), such as a local area network (LAN), wide area network (WAN), the Internet, or a combination thereof, connects the mobile devices, and the waste material analysis system 106. The waste material analysis system 106 may use a single server computer or multiple server computers operating in conjunction with one another, including, for example, a set of remote computers deployed as a cloud computing service.

Figure 2:
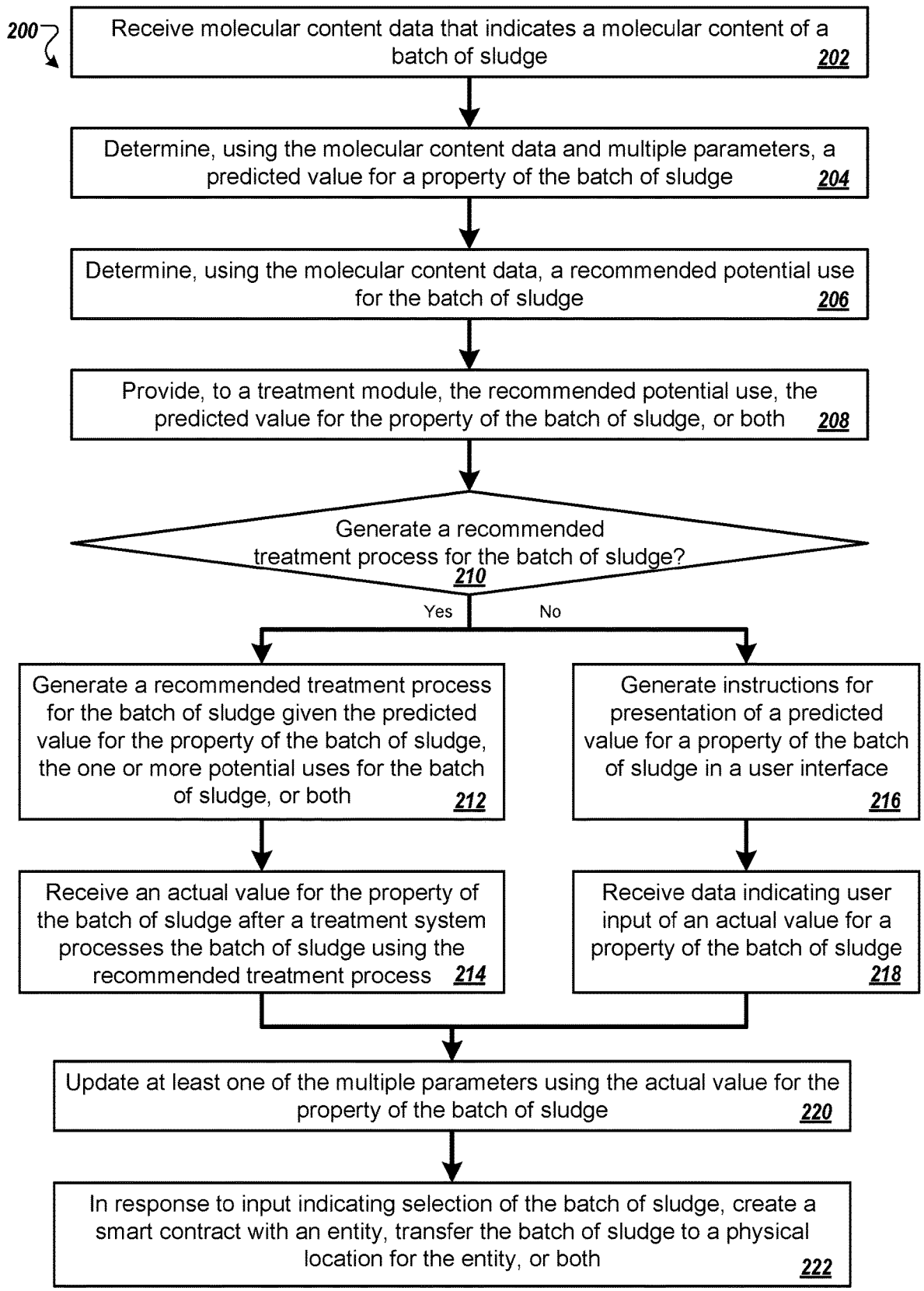
FIG. 2 is a flow diagram of a process 200 for updating parameters used in sludge analysis.

FIG. 2 is a flow diagram of a process 200 for updating parameters used in sludge analysis. For example, the process 200 can be used by the waste material analysis system 106 from the environment 100. Although the example described with reference to FIG. 2 refers to sludge, a system may use one or more steps of the process 200 for updating parameters for analysis of other types of waste material.

A waste material analysis system receives molecular content data that indicates a molecular content of a batch of sludge (202). For instance, the waste material analysis system receives the molecular content data from one or more sensors included in the waste analysis system or from another system, e.g., that includes one or more sensors. The sensors can scan the batch of sludge or a portion of the batch of sludge to determine the molecular content data for the scanned portion of the batch of sludge.

The waste material analysis system determines, using the molecular content data and multiple parameters, a predicted value for a property of the batch of sludge (204). The predicted value for the property may be for any property of the batch of sludge. For instance, the property may be a percentage of dry matter of the batch of sludge; a primary material included in the batch of sludge; a percentage of volatile solids included in the batch of sludge; a percentage of biogas material included in the batch of sludge; a percentage of organic matter included in the batch of sludge; a percentage of phosphorus included in the batch of sludge; a percentage of nitrogen included in a batch of sludge; a percentage of zinc included in the batch of sludge; a percentage of material included in the batch of sludge that can be reused; a predicted amount of usable material included in a batch of sludge; or a property that represents a combination of two or more of these. In some examples, a percentage of biogas may be represented by a percentage of methane included in a batch of sludge. The waste analysis system may include methane percentage as a property. A percentage of zinc may represent a percentage of heavy metals included in a batch of sludge. The waste analysis system may include heavy metals as a property. The predicted amount of usable material included in a batch of sludge may be determined based on a recommended use, a recommended destination, or both. For example, the predicted amount of usable material may indicate an amount of material included in a batch of sludge that can be used for a recommended use, a process at a recommended destination, or both. The predicted amount of usable material may indicate a predicted amount of material that can be extracted from a batch of sludge and used at a destination.

In some implementations, the waste material analysis system may determine chemical components included in a scanned portion of the batch of sludge using the molecular content data. The waste material analysis system can then use data about the chemical components to determine the predicted value for the property of the batch of sludge, e.g., as input to a model that determines the predicted value.

The waste material analysis system may determine predicted values for each of two or more properties for a batch of sludge. When determining predicted values for multiple properties, the waste material analysis system may determine multiple predicted values in parallel. For example, the waste material analysis system may use regression analysis, non-linear classification, or both, to determine the multiple predicted values in parallel. The waste material analysis system may determine all of the multiple predicted values concurrently. In some examples, the waste material analysis system may determine two of the multiple predicted values concurrently and then determine additional predicted values after determining at least one of the two predicted values.

The waste material analysis system determines, using the molecular content data, a recommended potential use for the batch of sludge (206). The waste material analysis system may use the predicted value for the property of the batch of sludge as input, in addition to or instead of, the molecular content data. In some implementations, the waste material analysis system may determine a recommended potential destination.

The waste material analysis system may use current weather conditions, predicted weather conditions, or both, to determine the recommended potential use for the batch of sludge. For instance, the waste material analysis system may determine multiple potential destinations for the batch of sludge. The waste material analysis system may use physical location information for each of the potential destinations to determine current weather conditions, predicted weather conditions, or both, for each of the multiple potential destinations. In some examples, when two of the potential destinations are physically located close to each other, e.g., in the same city, the waste material analysis system determines the current weather conditions, the predicted weather conditions, or both, for the two potential destinations at the same time, e.g., once.

The waste material analysis system can use the current weather conditions, the predicted weather conditions, or both, to determine a recommended potential use, a recommended potential destination, or both. For instance, when predicted weather conditions indicate that farm A will be dry and farm B will be wet, e.g., it will rain at farm B in two weeks but there will not be any rain at farm A in the next two weeks, the waste material analysis system may determine that farm A is a recommended destination for a batch of sludge with a high percentage of organic material and a low percentage of dry matter.

The waste material analysis system provides, to a treatment module, the recommended potential use, the predicted value for the property of the batch of sludge, or both (208). The waste material analysis system determines whether to generate a recommended treatment process for the batch of sludge (210). For example, the treatment module, or another module of the waste material analysis system, receives the predicted value, the recommended potential use, or both, from the waste material analysis system. The waste material analysis system may provide the recommended potential destination to the treatment module. In some examples, the waste material analysis system may provide the molecular content data to the treatment module.

The treatment module can use the received data to determine whether the batch of sludge should receive treatment processing. The treatment module may select a treatment process that has at least a threshold likelihood of improving a value for a property of the batch of sludge. The property may be the property to which the predicted value corresponds.

In response to determining to generate a recommended treatment process, the waste material analysis system generates a recommended treatment process for the batch of sludge given the predicted value for the property of the batch of sludge, the one or more potential uses for the batch of sludge, or both (212). For instance, the treatment module may use the received data as input to an artificial intelligence process to determine the recommended treatment process for the batch of sludge. In some implementations, the waste material analysis system may use current weather conditions, predicted weather conditions, or both, as input to the artificial intelligence process to determine the recommended treatment process for the batch of sludge.

The waste material analysis system receives an actual value for the property of the batch of sludge after a treatment system processes the batch of sludge using the recommended treatment process (214). For example, the waste material analysis system receives, from a treatment processing system, the actual value for the property. The treatment processing system may include one or more sensors used to capture the actual value for the property, e.g., as part of updated molecular content data for the batch of sludge after treatment.

The waste material analysis system generates instructions for presentation of a predicted value for a property of the batch of sludge in a user interface (216). The waste material analysis system may generate the instructions in response to determining not to generate a recommended treatment process. In some examples, the waste material analysis system may generate the instructions after receiving the actual value for the property of the batch of sludge, e.g., after performing step 214. The instructions may cause a device, e.g., a user device such as a mobile device, to present the predicted value in a user interface. The instructions may be for a web browser or another application. The waste material analysis system may generate the instructions and provide the instructions to a device to provide the predicted value for the property of the portion of the batch of sludge.

In some implementations, the user interface can include information about multiple different batches of sludge, including the batch of sludge for which the predicted value of the property was determined. Each of the multiple different batches of sludge may have a corresponding predicted value for the property. The user interface can include a filter option to enable a user, e.g., interacting with the user interface, to filter details about batches of sludge given values of the properties of the batches of sludge. For instance, the filter may enable the user to filter the presented details based on the property and the corresponding predicted values for the property of the respective batch of sludge. The user interface can enable a user to select a batch of sludge for delivery to a destination.

In some implementations, the waste material analysis system may provide the instructions to a system for the recommended potential destination. For instance, the waste material analysis system may provide the instructions to a computer operated on behalf of or for the recommended potential destination.

In some implementations, the waste material analysis system may provide other data, instead of instructions, to the system for the recommended potential destination. The data may be part of an automated transaction process used to determine whether to send the batch of sludge to a physical location for the recommend potential destination.

The waste material analysis system receives data indicating user input of an actual value for a property of the batch of sludge (218). For example, the data indicating the user input may indicate the actual value for the property upon request that the batch of sludge be delivered to a destination, upon delivery, after the batch of sludge was used at a destination, or a combination of two or more of these. In some implementations, when the property is a sale value, the predicted value is a predicted sale value and the actual value is the actual sale value for a batch of sludge. In some implementations, when the waste material analysis system generates a recommended treatment process and generates instructions for presentation of a predicted value, the predicted value used to determine the treatment process may be the same value as the predicted value indicated by the instructions, e.g., the waste material analysis system may determine a single predicted value. In some implementations, when the waste material analysis system generates a recommended treatment process and generates instructions for presentation of a predicted value, the predicted value used to determine the treatment process may be a different predicted value than the predicted value indicated by the instructions. The different predicted values may be for the same property, e.g., a percentage of organic matter, or for different properties.

The waste material analysis system updates at least one of the multiple parameters using the actual value for the property of the batch of sludge (220). The waste material analysis system, e.g., a machine learning module, may update at least one of the multiple parameters using the actual value for a first property received after the treatment system processes the batch of sludge, using the data indicating the user input of the actual value for a second property, or both. For example, the waste material analysis system may update at least one of the multiple parameters as part of a reinforcement learning process.

In response to input indicating selection of the batch of sludge, the waste material analysis system creates a smart contract with an entity, transfers the batch of sludge to a physical location for the entity, or both (222). The input may indicate user input of a selection of a batch of sludge, e.g., on a trading platform. The entity may employ the user. The input may indicate an automated system, e.g., used by the entity, determining that the batch of sludge should be delivered to a physical location for the entity, e.g., a destination at which the entity can use the batch of sludge.

The smart contract may be any appropriate type of smart contract and may indicate an intent to transfer the batch of sludge from a first physical location, e.g., a waste processing facility, to a second location, e.g., for the entity. The smart contract may be a blockchain contract.

Transfer of the batch of sludge to the physical location may include physically placing the batch of sludge on a transport mechanism, e.g., a vehicle, to deliver the batch of sludge to the physical location. The batch of sludge may be transferred using any appropriate methods. The entity may be an entity purchasing the batch of sludge.

In some implementations, the input indicating selection of the batch of sludge may be the data indicating the user input of the actual value for the property of the batch of sludge. For instance, when the actual value is an actual price paid offered by the entity to purchase the batch of sludge, the waste material analysis system may, in response to receipt of the actual value, create the smart contract, initiate transfer of the batch of sludge, or both.

Initiation of transfer of the batch of sludge may include the waste material analysis system sending instructions to a transportation system to initiate the transfer of the batch of sludge. The transportation system may receive the instructions and use the instructions to retrieve the batch of sludge and deliver the batch of sludge to the physical location for the entity.

The order of steps in the process 200 described above is illustrative only, and updating the parameters used in the sludge analysis can be performed in different orders. For example, the waste material analysis system may determine the recommended potential use and then determine the predicted value for the property of the batch of sludge. In some examples, the waste material analysis system may determine, concurrently, the recommended potential use and the predicted value for the property of the batch of sludge. For instance, the waste material analysis system may use a single module that receives the molecular content data as input and determines both the recommended potential use and the predicted value. Instead of or in addition to determining the recommended potential use, the waste material analysis system may determine a recommended potential destination. In some implementations, the waste material analysis system may receive the data indicating the user input of the actual value after or concurrently with creation of the smart contract, transfer of the batch of sludge to the physical location, or both.

In some implementations, the process 200 can include additional steps, fewer steps, or some of the steps can be divided into multiple steps. For example, the waste material analysis system may receive the molecular content data, determine the predicted value, and provide the predicted value, e.g., to a treatment module, without performing the other steps of the process 200. In some implementations, the waste material analysis system may perform these steps and then receive the actual value, and update at least one of the multiple parameters.

In some implementations, a waste material processing facility may include one or more sensors, e.g., near infrared spectrometers. For example, a sewerage treatment works may include the one or more sensors. The sensors at the waste material processing facility may scan waste material, e.g., at regular intervals, to determine molecular content data for the waste material. The waste material processing facility may determine a batch of waste material, e.g., that is physical grouped together. Each batch may have a predetermined size, e.g., the same size, or at most a predetermined size. One set of molecular content data captured during one of the intervals may be for a single batch or multiple batches of waste material.

The waste material processing facility may send, to a cloud service that includes a waste material analysis system, the molecular content data. The waste material processing facility may use an API to send the molecular content data to the cloud service. In some examples, the waste material processing facility, e.g., a user at the waste material processing facility, may use an application installed on a device, e.g., a mobile device, to send the molecular content data to the cloud service. The mobile device can receive the molecular content data from the sensors.

The cloud service can use the molecular content data as input to a module to determine the chemical components of the scanned waste material. The cloud service can use data for the chemical components, the molecular content data, or both, as input to one or more modules to determine a predicted value for a property of the batch of waste material, a recommended treatment process, a recommend use for the batch of waste material, a recommended destination for the batch of waste material, or a combination of two or more of these. In some examples, the predicted value can be a recommend sale price, or a minimum initial bidding price for purchase of the batch of waste material. The cloud service may determine a recommended treatment process specific to the waste material processing facility and the treatment processes available at the waste material processing facility.

The cloud service may determine a recommended treatment process based on a likelihood that the recommended treatment process will maximize a quantity of target chemicals, e.g., target materials, included in the batch of waste material, maximize a quality of target chemicals included in the batch of waste material, or both. For example, the cloud service may analyze multiple potential treatment processes and the molecular content data to determine a recommended treatment process with a highest likelihood of maximizing a quantity, quality, or both, of material in the batch of waste material. The cloud service may use a recommended use, a recommended destination, or both, to determine particular material in the batch of waste material for which the treatment process should maximize the quantity, quality, or both.

In some implementations, the cloud service may use market data, treatment site data, or both, to determine the predicted value, the treatment process, or both. For instance, the cloud service may use a demand, e.g., a local demand, current prices or price trends, treatment process available at the waste material processing facility, or a combination of two or more of these, to determine the predicted value, the recommended treatment process, the recommended use, the recommended destination, or a combination of two or more of these.

The waste material processing facility receives, from the cloud service, data for the predicted value for the property, the recommended treatment process, the recommended use, the recommended destination, or a combination of two or more of these. The waste material processing facility may present, in a user interface, some or all of the received data. For example, a device for the waste material processing facility, e.g., physically at a physical location of the waste material processing facility or at another physical location, may present the predicted value for the property, the recommended treatment process, the recommended use, recommended destination, or a combination of two or more of these. The device that presents some or all of the received data may be the same device that provided the molecular content data to the cloud service or a different device.

In some implementations, the waste material processing facility may provide at least some of the data to a trading platform to allow a third party, e.g., associated with a potential destination such as a recommended destination, to purchase a batch of waste material. The trading platform may be a bidding platform, e.g., based on a minimum bid price, a sales platform, e.g., based on a listed sale price, or a combination of both.

The waste material processing facility may automatically provide data for a batch of waste material to the trading platform, may automatically create a contract for a sale of a batch of waste material, may automatically facilitate transportation of a batch of waste material to a destination, or a combination of two or more of these.

The waste material processing facility or another system may create a smart contract using a blockchain process. Use of a blockchain process may improve security of sales transactions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a smart phone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HyperText Markup Language (HTML) page, to a user device, e.g., for purposes of displaying data to and receiving user input from a user interacting with the user device, which acts as a client. Data generated at the user device, e.g., a result of the user interaction, can be received from the user device at the server.

Figure 3:
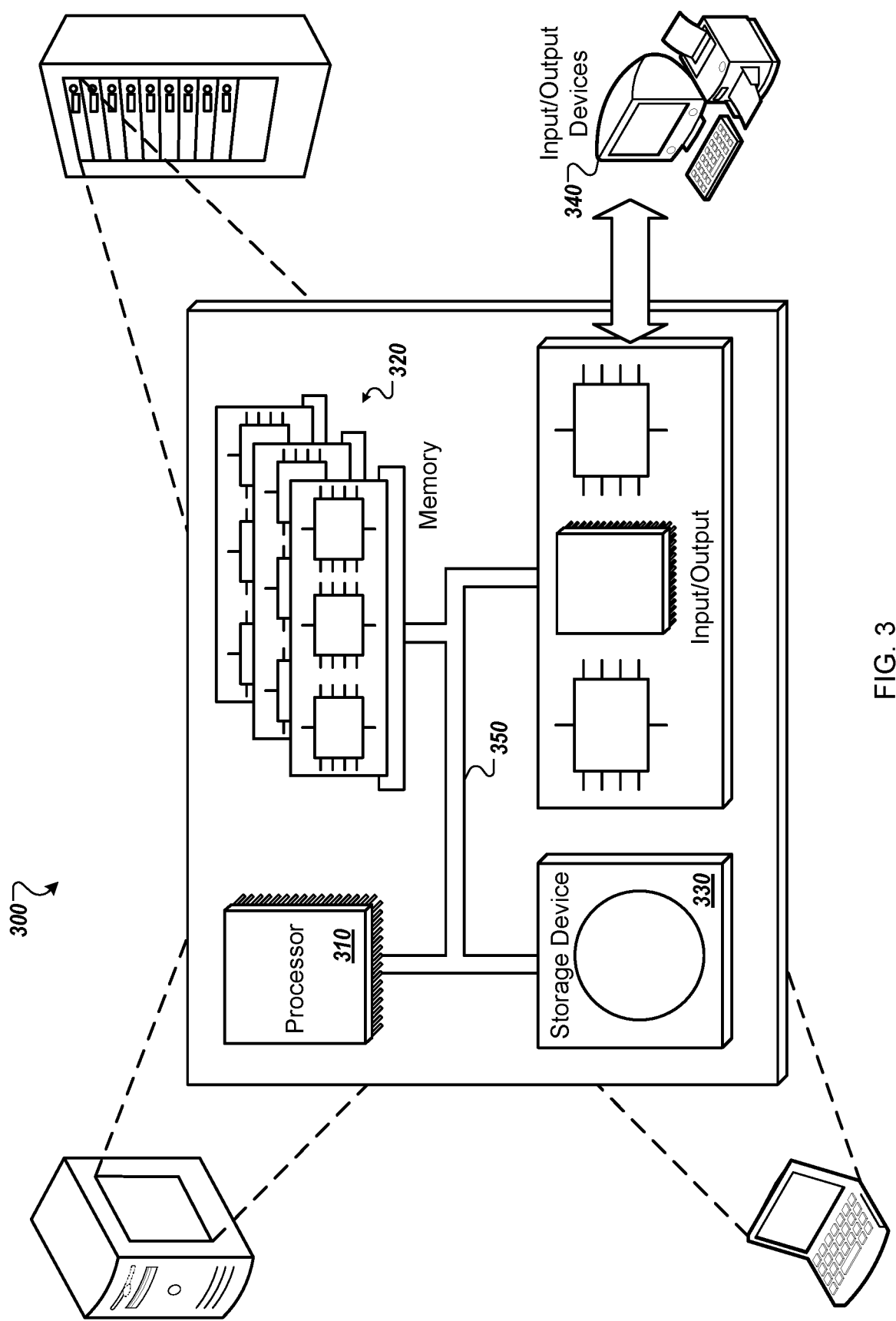
FIG. 3 is a block diagram of a computing system that can be used in connection with computer-implemented methods described in this document.

An example of one such type of computer is shown in FIG. 3, which shows a schematic diagram of a generic computer system 300. The system 300 can be used for the operations described in association with any of the computer-implemented methods described previously, according to one implementation. The system 300 includes a processor 310, a memory 320, a storage device 330, and an input/output device 340. Each of the components 310, 320, 330, and 340 are interconnected using a system bus 350. The processor 310 is capable of processing instructions for execution within the system 300. In one implementation, the processor 310 is a single-threaded processor. In another implementation, the processor 310 is a multi-threaded processor. The processor 310 is capable of processing instructions stored in the memory 320 or on the storage device 330 to display graphical information for a user interface on the input/output device 340.

The memory 320 stores information within the system 300. In one implementation, the memory 320 is a computer-readable medium. In one implementation, the memory 320 is a volatile memory unit. In another implementation, the memory 320 is a non-volatile memory unit.

The storage device 330 is capable of providing mass storage for the system 300. In one implementation, the storage device 330 is a computer-readable medium. In various different implementations, the storage device 330 may be a floppy disk device, a hard disk device, an optical disk device, or a tape device.

The input/output device 340 provides input/output operations for the system 300. In one implementation, the input/output device 340 includes a keyboard and/or pointing device. In another implementation, the input/output device 340 includes a display unit for displaying graphical user interfaces.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising one or more computers and one or more storage devices on which are stored instructions that are operable, when executed by the one or more computers, to cause the one or more computers to perform operations comprising:
   receiving molecular content data that indicates a molecular content of a portion of a batch of sludge;
   determining, by a machine learning module included in the system using the molecular content data and multiple parameters, a predicted value for a property of the portion of the batch of sludge, the predicted value representing an expected value for the property if one or more actions associated with the batch of sludge were to occur;
   providing the predicted value for the property of the portion of the batch of sludge; and
   after determining the predicted value for the property of the portion of the batch of sludge:
      receiving an actual value for the property of the portion of the batch of sludge after occurrence of the one or more actions; and
      updating, by the machine learning module and using the actual value for the property of the portion of the batch of sludge, at least one of the multiple parameters used by the machine learning module to determine the predicted value for the property of the portion of the batch of sludge.

2. The system of claim 1, wherein receiving the molecular content data that indicates the molecular content of the batch of sludge comprises receiving, from a near infrared spectrometer, near-infrared spectroscopy data.

3. The system of claim 2, comprising the near infrared spectrometer.

4. The system of claim 3, the operations comprising:
   scanning, by the near infrared spectrometer, the batch of sludge to determine the molecular content data.

5. The system of claim 1, wherein determining, by the machine learning module included in the system using the molecular content data and the multiple parameters, the predicted value for the property of the portion of the batch of sludge comprises determining, in parallel by the machine learning module for each of two or more properties of the batch of sludge, a predicted value for the respective property.

6. The system of claim 5, wherein determining, in parallel by the machine learning module for each of the two or more properties of the batch of sludge, the predicted value for the respective property comprises determining, for each of the two or more properties of the batch of sludge using regression analysis, the predicted value for the respective property.

7. The system of claim 5, wherein determining, in parallel by the machine learning module for each of the two or more properties of the batch of sludge, the predicted value for the respective property comprises determining, for each of the two or more properties of the batch of sludge using non-linear classification, the predicted value for the respective property.

8. The system of claim 1, wherein determining, by the machine learning module included in the system using the molecular content data and the multiple parameters, the predicted value for the property of the portion of the batch of sludge comprises determining the predicted value for the property of the portion of the batch of sludge using the molecular content data, the multiple parameters, and one or more potential uses for the batch of sludge.

9. The system of claim 1, wherein determining, by the machine learning module included in the system using the molecular content data and the multiple parameters, the predicted value for the property of the portion of the batch of sludge comprises determining, by the machine learning module, the predicted value using, as input to the machine learning module, characteristics of a potential purchaser, environmental parameters, or both.

10. The system of claim 1, wherein determining, by the machine learning module included in the system using the molecular content data and the multiple parameters, the predicted value for the property of the portion of the batch of sludge comprises determining at least one of:
a predicted value for a percentage of dry matter of the batch of sludge;
a predicted value for a percentage of a primary material included in the batch of sludge;
a predicted value for a percentage of volatile solids included in the batch of sludge;
a predicted value for a percentage of biogas material included in the batch of sludge;
a predicted value for a percentage of organic matter included in the batch of sludge;
a predicted value for a percentage of phosphorus included in the batch of sludge;
a predicted value for a percentage of zinc included in the batch of sludge; or
a predicted value for a percentage of material included in the batch of sludge that can be reused.

11. The system of claim 1, wherein:
providing the predicted value for the property of the portion of the batch of sludge comprises providing, to a treatment module, the predicted value for the property of the portion of the batch of sludge to cause the treatment module to determine a recommended treatment process for the batch of sludge given the predicted value for the property of the portion of the batch of sludge and one or more potential uses for the batch of sludge; and
receiving the actual value for the property of the portion of the batch of sludge comprises receiving the actual value for the property of the portion of the batch of sludge after a treatment system processes the batch of sludge using the recommended treatment process.

12. The system of claim 11, the operations comprising:
determining, using the molecular content data and from two or more potentials uses for the batch of sludge, a recommended potential use for the batch of sludge, wherein:
providing, to the treatment module, the predicted value for the property of the portion of the batch of sludge comprises providing, to the treatment module, the recommended potential use and the predicted value for the property of the portion of the batch of sludge to cause the treatment module to determine a recommended treatment process for the batch of sludge given the predicted value for the property of the portion of the batch of sludge and the recommended potential use determined from the two or more potential uses for the batch of sludge.

13. The system of claim 12, the operations comprising:
determining, by the treatment module, the recommended treatment process for the batch of sludge given the predicted value for the property of the portion of the batch of sludge and the recommended potential use determined from the two or more potential uses for the batch of sludge.

14. The system of claim 1, wherein:
providing the predicted value for the property of the portion of the batch of sludge comprises generating instructions for presentation of the predicted value for the property of the portion of the batch of sludge in a user interface; and
receiving the actual value for the property of the portion of the batch of sludge comprises receiving data indicating user input of the actual value for the property of the portion of the batch of sludge.

15. The system of claim 14, wherein generating the instructions for presentation of the predicted value for the property of the portion of the batch of sludge in a user interface comprises generating the instructions for presentation of a user interface that includes a filter option to enable a user to view details about multiple different batches of sludge, including the batch of sludge, and to filter details about batches of sludge using the predicted value for the property of the portion of the respective batch of sludge.

16. The system of claim 14, wherein generating instructions for presentation of the predicted value for the property of the portion of the batch of sludge in a user interface comprises enabling a user to select the batch of sludge for purchase.

17. The system of claim 14, wherein generating instructions for presentation of the predicted value for the property of the portion of the batch of sludge in a user interface comprises enabling a user to select the batch of sludge for purchase using a blockchain smart contract.

18. A non-transitory computer storage medium encoded with instructions that, when executed by one or more computers, cause the one or more computers to perform operations comprising:
receiving molecular content data that indicates a molecular content of a portion of a batch of sludge;
determining, by a machine learning module implemented on the one or more computers using the molecular content data and multiple parameters, a predicted value for a property of the portion of the batch of sludge, the predicted value representing an expected value for the property if one or more actions associated with the batch of sludge were to occur;
providing the predicted value for the property of the portion of the batch of sludge; and
after determining the predicted value for the property of the portion of the batch of sludge:
receiving an actual value for the property of the portion of the batch of sludge after occurrence of the one or more actions; and
updating, by the machine learning module and using the actual value for the property of the portion of the batch of sludge, at least one of the multiple parameters used by the machine learning module to determine the predicted value for the property of the portion of the batch of sludge.

19. A computer-implemented method comprising:
receiving molecular content data that indicates a molecular content of a portion of a batch of sludge;
determining, by a machine learning module implemented on one or more computers using the molecular content data and multiple parameters, a predicted value for a property of the portion of the batch of sludge, the predicted value representing an expected value for the property if one or more actions associated with the batch of sludge were to occur;
providing the predicted value for the property of the portion of the batch of sludge; and
after determining the predicted value for the property of the portion of the batch of sludge:
receiving an actual value for the property of the portion of the batch of sludge after occurrence of the one or more actions; and
updating, by the machine learning module and using the actual value for the property of the portion of the batch of sludge, at least one of the multiple parameters used by the machine learning module to determine the predicted value for the property of the portion of the batch of sludge.

20. A system comprising one or more computers and one or more storage devices on which are stored instructions that are operable, when executed by the one or more computers, to cause the one or more computers to perform operations comprising:
receiving molecular content data that indicates a molecular content of a portion of a batch of sludge;
determining, by a machine learning module included in the system, a predicted value for a property of the portion of the batch of sludge after treatment i) using the molecular content data and multiple parameters and one or more potential uses for the batch of sludge, and ii) using, as input to the machine learning module, characteristics of a potential purchaser, environmental parameters, or both, the predicted value for the property of the portion of the batch of sludge comprising at least one of:
a predicted value for a percentage of dry matter of the batch of sludge;
a predicted value for a percentage of a primary material included in the batch of sludge;
a predicted value for a percentage of volatile solids included in the batch of sludge;
a predicted value for a percentage of biogas material included in the batch of sludge;
a predicted value for a percentage of organic matter included in the batch of sludge;
a predicted value for a percentage of phosphorus included in the batch of sludge;
a predicted value for a percentage of zinc included in the batch of sludge; or
a predicted value for a percentage of material included in the batch of sludge that can be reused;
providing the predicted value for the property of the portion of the batch of sludge; and
after determining the predicted value for the property of the portion of the batch of sludge:
receiving an actual value for the property of the batch of sludge; and
updating, by the machine learning module and using the actual value for the property of the portion of the batch of sludge, at least one of the parameters using the actual value for the property of the batch of sludge.

21. The system of claim 1, wherein the one or more actions comprise at least one of treatment of the batch of sludge, delivery of the batch of sludge to a destination, use of the batch of sludge at the destination, and sale of the batch of sludge.

* * * * *